United States Patent
Döring

(10) Patent No.: US 6,740,874 B2
(45) Date of Patent: May 25, 2004

(54) ION MOBILITY SPECTROMETER WITH MECHANICALLY STABILIZED VACUUM-TIGHT X-RAY WINDOW

(75) Inventor: Hans-Rüdiger Döring, Leipzig (DE)

(73) Assignee: Bruker Saxonia Analytik GmbH, Leipzig (DE)

(*) Notice: Subject to any disclaimer, the term of this patent is extended or adjusted under 35 U.S.C. 154(b) by 0 days.

(21) Appl. No.: 10/132,066

(22) Filed: Apr. 25, 2002

(65) Prior Publication Data
US 2002/0185594 A1 Dec. 12, 2002

(30) Foreign Application Priority Data
Apr. 26, 2001 (DE) .......... 101 20 335

(51) Int. Cl.[7] ............................. H01J 47/40
(52) U.S. Cl. .......... 250/287; 250/281; 250/282; 250/286; 250/288; 250/423 P; 250/423 R; 436/173; 436/181
(58) Field of Search ............ 250/281, 282, 250/286–288, 423 P, 423 R; 436/173, 181

(56) References Cited

U.S. PATENT DOCUMENTS

| | | | | |
|---|---|---|---|---|
| 5,130,539 A | * | 7/1992 | Canter | 250/306 |
| 5,416,821 A | * | 5/1995 | Frazier et al. | 378/154 |
| 5,585,644 A | * | 12/1996 | Van Der Borst | 250/505.1 |
| 5,968,837 A | * | 10/1999 | Doring et al. | 436/173 |
| 5,969,349 A | * | 10/1999 | Budovich et al. | 250/286 |
| 6,100,521 A | * | 8/2000 | Doring et al. | 250/286 |
| 6,107,624 A | * | 8/2000 | Doring et al. | 250/286 |
| 6,233,306 B1 | * | 5/2001 | Van Sprang | 378/35 |
| 6,359,952 B1 | * | 3/2002 | Alvord | 376/202 |
| 6,429,426 B1 | * | 8/2002 | Doring | 250/288 |
| 6,477,226 B1 | * | 11/2002 | Lehmann et al. | 378/44 |
| 6,586,729 B2 | * | 7/2003 | Doring | 250/287 |
| 2002/0185594 A1 | * | 12/2002 | Doring | 250/287 |

FOREIGN PATENT DOCUMENTS

| | | | | |
|---|---|---|---|---|
| DE | 19933650 C1 | * | 3/2001 | G01N/23/00 |
| GB | 2 315 154 A | | 1/1998 | |
| GB | 2 315 155 A | | 1/1998 | |

* cited by examiner

Primary Examiner—John R. Lee
Assistant Examiner—Bernard Souw

(57) ABSTRACT

An ion mobility spectrometer (IMS) has a non-radioactive electron source and an x-ray anode in an evacuated chamber. The impinging of electrons from the source on the anode results in the generation of x-ray radiation. The x-ray radiation passes through a window that provides a vacuum barrier between the electron source chamber and a reaction chamber of the IMS by an x-ray window. A support grid is attached to the reaction-chamber side of the x-ray window, and mechanically stabilizes the window.

16 Claims, 1 Drawing Sheet

ION MOBILITY SPECTROMETER WITH MECHANICALLY STABILIZED VACUUM-TIGHT X-RAY WINDOW

FIELD OF THE INVENTION

The invention relates generally to ion mobility spectrometry and, more specifically, to ion mobility spectrometers having a window providing a vacuum barrier between a source chamber and a reaction chamber.

BACKGROUND OF THE INVENTION

In one type of ion mobility spectrometer (IMS), an evacuated electron source chamber contains a non-radioactive electron source. The electron source and an x-ray anode are connected to an accelerating voltage source in such a way that electrons from the source impinge upon the anode, causing the generation of x-ray radiation. These x-rays enter an adjacent reaction chamber of the IMS through a gas-tight x-ray window which is impermeable to electrons from the electron source. The x-rays passing through the window then react with and ionize the molecules of a sample material in the reaction chamber. This type of IMS is known from U.S. patent Ser. No. 09/617,716, which is incorporated herein by reference in its entirety.

SUMMARY OF THE INVENTION

In accordance with the present invention, an ion mobility spectrometer is provided that uses a gas-tight window between an evacuated electron source chamber and a reaction chamber, and that provides the window with a support grid attached to the reaction chamber side of the window. Within the electron source chamber is a non-radioactive electron source connected to the negative side of an accelerating voltage source, and an x-ray anode connected to the positive side of the accelerating voltage. The operation of the electron source and the anode are such that x-ray radiation is generated by electrons from the electron source impinging upon the anode. The x-ray radiation passes through the window into the reaction chamber, where it is ionizes material therein. In the invention, the window is stabilized by the support grid, allowing the window to be thinner and of a greater diameter than would otherwise be possible. Preferably, there is a permanent metal bond between the support grid and the x-ray window. Substantially no electrons from the electron source impinge on the support grid, as might otherwise cause undesirable bremsstrahlung. However, in an illustrative embodiment, x-ray radiation does pass through the window to impinge on the support grid and may produce desired photoelectrons for ionization in the reaction chamber.

The x-ray window may comprise beryllium and may have a thickness of between 5 $\mu$m and 50 $\mu$m and an effective diameter of between 3 mm and 20 mm. Beryllium is traditionally used as window material in x-ray applications because of its low atomic number. At the stated thicknesses or diameters, the mechanical stability of the window without a support grid could fail at a pressure differential as low as approximately 1 bar.

In one embodiment, the anode in the electron source chamber is positioned relative to the x-ray window such that none of the electrons emerging from the electron source reach the x-ray window. This is achieved, for example, by an arrangement where the electrons are accelerated approximately parallel to the partition toward the anode where they arrive at an angle of approximately 45° and produce the x-ray radiation (characteristic radiation and/or bremsstrahlung). Only x-ray radiation impacts on the x-ray window, which is therefore unaffected by electrons.

In another embodiment, the x-ray anode may be attached to the vacuum side (i.e., the electron source side) of the x-ray window as a thin layer (e.g., less than 500 nm) so that electrons arriving from the electron source are decelerated in the metal layer and produce x-ray radiation that passes through the x-ray window. In one embodiment, the thickness of such a metal layer is at least seven half-value thicknesses of the electrons penetrating from the electron source, so that substantially no electrons reach the x-ray window directly. In addition, the thermal load is significantly moderated due to the conductivity of the metal layer. It may also be desirable to make the metal layer thin enough that it does not exceed two half-value thicknesses of the x-ray radiation produced. This ensures that the x-ray radiation penetrating through the x-ray window into the reaction chamber is still sufficiently intense. In such an embodiment, the support grid on the other side of the window does not disturb the coating of anode material, or interfere with its application.

The anode material may comprise metals with high atomic number such as tungsten or gold. In such a case, bremsstrahlung is predominantly exploited. However, light elements may also be used, such as aluminum or magnesium, whose characteristic radiation is within a very favorable range so that air components in the reaction chamber, predominantly nitrogen and oxygen, are ionized via their K shells at approx 400 to 500 eV with a large cross-section.

The preferred accelerating voltage is less than 5 kV. This energy level should be sufficient to generate x-ray radiation that penetrates the window and is able to achieve ionization in the reaction chamber, either directly or via photoelectrons. The range in air at atmospheric pressure is largely adapted to the geometric dimensions of the reaction chamber (roughly in the centimeter range). Moreover, these voltage levels can be handled easily and without the need for extreme safety precautions.

DETAILED DESCRIPTION

Figures 1, 2:
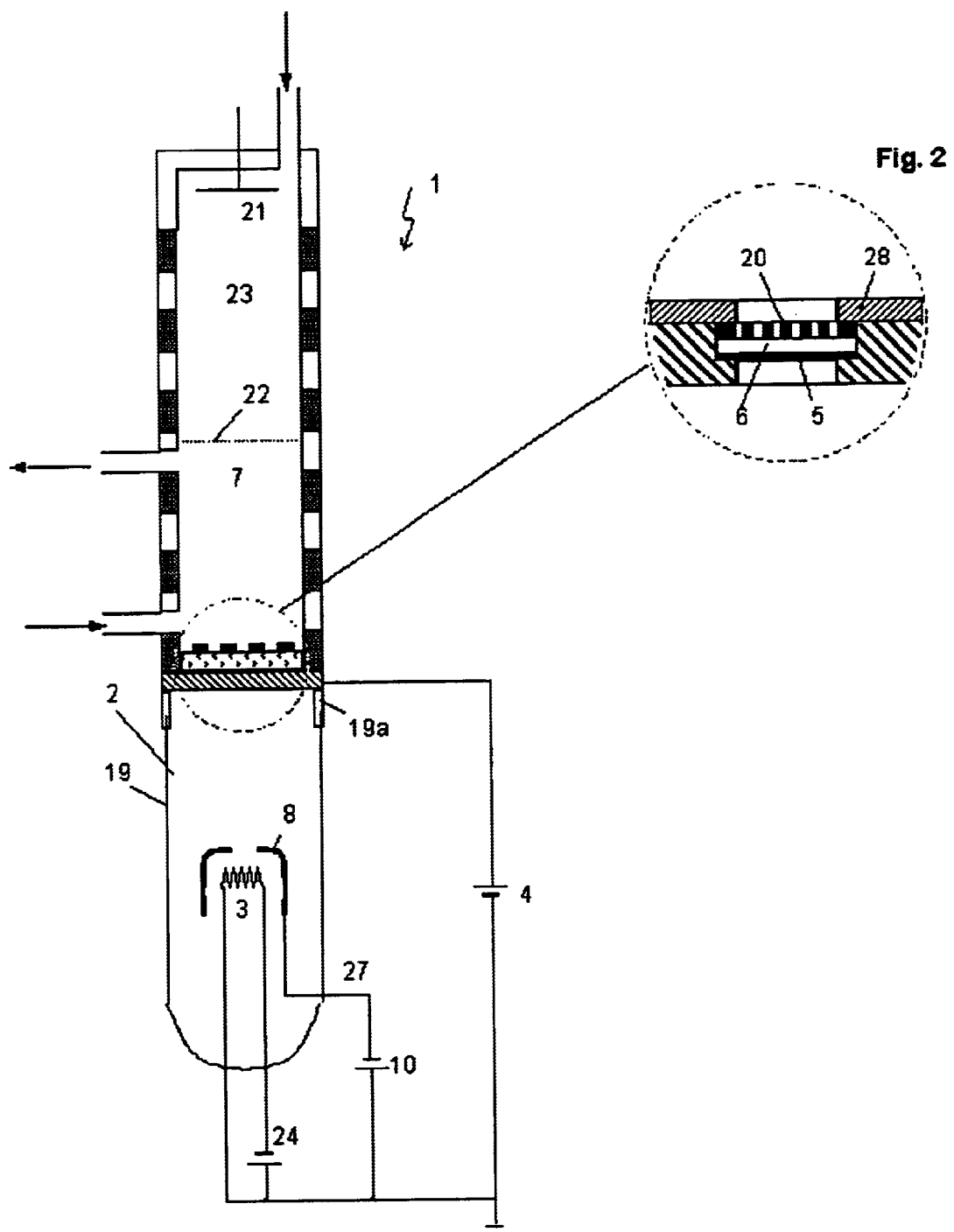
FIG. 1 is a schematic arrangement of an IMS according to the invention.
FIG. 2 is a detailed schematic drawing of the x-ray window of the IMS shown in FIG. 1.

FIG. 1 is a detailed schematic representation of an ion mobility spectrometer (IMS) 1 with an evacuated electron source chamber 2 and an adjacent reaction chamber 7. This spectrometer is similar to that shown in U.S. patent Ser. No. 09/617,716, which is incorporated by reference herein in its entirety. In the system shown in FIG. 1, the reaction chamber 7 is separated from a drift chamber 23 by a switchable grid 22, and at the end of the drift chamber 23 is ion detector 21. The electron source chamber 2 and reaction chamber 7 are separated by a vacuum-tight x-ray window 6 made from beryllium. The window 6 has a thickness of 10 $\mu$m and an accessible diameter of 10 mm. On the vacuum-chamber side the x-ray window 6 is a 100 nm thick vapor deposited aluminum coating 5. The window is retained on the reaction-chamber side by a honeycomb support grid 20 made of nickel. The mesh width of the honeycomb is 300 $\mu$m, the transparency is 80% and the thickness is 50 $\mu$m. The nickel grid 20 is grown onto the beryllium window 6 by electrodeposition and therefore bonded fast to it.

The electron source chamber 2 has a stainless steel housing 19. The electron source chamber contains a thermionic cathode 3, which serves as a non-radioactive electron source and is connected to a variable, electronically controllable filament voltage source 24 via insulated, vacuum-tight feed-throughs. In operation, there is an accelerating voltage provided by voltage source 4 of 1.8 kV between the anode 5 and the filament voltage source 24. Between the thermionic cathode 3 and the anode 5, there is a control electrode 8 in the form of a Wehnelt cylinder. A voltage source 10 is located between the control electrode 8 and the filament voltage source 24. The control electrode voltage is supplied via an insulated feed-through 27 and can be controlled between −5V and −50V. The length of the electron-source chamber 2 is 50 mm and its external diameter is 20 mm.

FIG. 2 shows an isolated view of one illustrative embodiment of a window 6 between the reaction chamber 7 and the electron source chamber 2. The broken lines in FIGS. 1 and 2 indicate the location of the window assembly relative to the apparatus of FIG. 1. In this embodiment, the window is 10 $\mu$m thick and has a 100 nm thick aluminum anode 5, which is vapor deposited onto the surface of the window facing the evacuated electron source chamber. A 50 $\mu$m thick honeycomb nickel support grid 20 is located on the reaction chamber side of the window 6, and has approximately 80% transmission. The nickel support grid 20 is grown onto the beryllium window 6 by electrodeposition. The grid is soldered to a ring-shaped stainless steel disk 28 at the edge. The sandwich consisting of anode 5, window 6, support grid 20 and stainless steel ring 28 is inserted into an appropriate retainer for the x-ray window in the partition between the reaction chamber 7 and the electron source chamber 2, which has been cut out for this purpose. The sandwich is soldered in so that it is mechanically fixed and vacuum tight.

It is claimed:

1. An ion mobility spectrometer comprising:
   an evacuated electron source chamber;
   a reaction chamber separated from the electron source chamber by a gas-tight x-ray window that is substantially impermeable to electrons generated by the electron source;
   a non-radioactive electron source and an x-ray anode located within the electron source chamber such that electrons from the electron source impinge upon the anode to cause x-ray radiation to be generated toward the window; and
   a support grid attached to a side of the x-ray window facing the reaction chamber, the support grid mechanically stabilizing the window.

2. The ion mobility spectrometer of claim 1 wherein a housing of the electron source chamber comprises metal.

3. The ion mobility spectrometer of claim 2 wherein the housing comprises stainless steel.

4. The ion mobility spectrometer of claim 1, wherein the x-ray window comprises beryllium.

5. The ion mobility spectrometer of claim 1, wherein there is a substantially permanent metal bond between the support grid and the x-ray window.

6. The ion mobility spectrometer of claim 1, wherein the x-ray window comprises a thickness of between 5 $\mu$m and 50 $\mu$m and an accessible diameter of between 3 mm and 20 mm.

7. The ion mobility spectrometer of claim 1 wherein the anode is physically separated from the x-ray window.

8. The ion mobility spectrometer of claim 1 wherein the anode comprises a coating on the side of the window facing the electron source chamber.

9. The ion mobility spectrometer of claim 8 wherein the coating has a thickness of less than 500 nm.

10. The ion mobility spectrometer of claim 1 wherein the electron source is connected to the negative pole of an accelerating voltage source and the anode is connected to the positive pole of the accelerating voltage source.

11. The ion mobility spectrometer of claim 1 wherein the accelerating voltage is less than 5 kV.

12. An ion mobility spectrometer comprising:
    an evacuated electron source chamber;
    a reaction chamber separated from the electron source chamber by a gas-tight x-ray window that is substantially impermeable to electrons generated by the electron source, the window having a thickness of between 5 $\mu$m and 50 $\mu$m, and having an accessible diameter of between 3 mm and 20 mm;
    a non-radioactive electron source and an x-ray anode located within the electron source chamber such that electrons from the electron source impinge upon the anode to cause x-ray radiation to be generated toward the window;
    a voltage source having a negative pole connected to the electron source and a positive pole connected to the anode, the voltage source providing an accelerating voltage potential between the electron source and the anode; and
    a support grid attached, by a substantially permanent metal bond, to a side of the x-ray window facing the reaction chamber, the support grid mechanically stabilizing the window.

13. The ion mobility spectrometer of claim 12 wherein the anode is physically separate from the window.

14. The ion mobility spectrometer of claim 12 wherein the anode comprises a coating on the side of the window facing the electron source chamber.

15. The ion mobility spectrometer of claim 14 wherein the coating has a thickness of less than 500 nm.

16. The ion mobility spectrometer of claim 12 wherein the accelerating voltage is less than 5 kV.

* * * * *